United States Patent [19]
Jorgensen et al.

[11] 3,964,297
[45] June 22, 1976

[54] ULTRASONIC INSPECTION APPARATUS

[75] Inventors: Hans G. Jorgensen; B. Wendell Hautaniemi, both of Ithaca, N.Y.

[73] Assignee: Ithaco, Incorporated, Ithaca, N.Y.

[22] Filed: Dec. 16, 1974

[21] Appl. No.: 532,889

[52] U.S. Cl. .............................. 73/67.8 R; 73/67.9
[51] Int. Cl.² .................................. G01N 29/04
[58] Field of Search............. 73/67.7, 67.8 R, 67.8 S, 73/67.9

[56] References Cited
UNITED STATES PATENTS

| | | | |
|---|---|---|---|
| 3,722,263 | 3/1973 | Hautaniemi et al. | 73/67.8 S |
| 3,780,572 | 12/1973 | Rocha | 73/67.7 X |
| 3,805,597 | 4/1974 | Ohta et al. | 73/67.9 |
| 3,817,089 | 6/1974 | Eggleton et al. | 73/67.8 S |
| 3,823,603 | 7/1974 | Couture | 73/67.9 |
| 3,827,287 | 8/1974 | Boggs et al. | 73/67.8 S |
| 3,895,525 | 7/1975 | Eichelberger et al. | 73/67.9 |

*Primary Examiner*—Herbert Goldstein
*Assistant Examiner*—John P. Beauchamp
*Attorney, Agent, or Firm*—Richard G. Stephens

[57] ABSTRACT

Trains of echo signals occurring from repetitively transmitted ultrasonic pulses are stored in a shift register in accordance with their times of occurrence, and the stages of the shift register are connected to illuminate respective light-emitting diodes arranged in a linear array, providing a display indicating the depths of density changes in animal matter or the like being inspected.

27 Claims, 14 Drawing Figures

ULTRASONIC INSPECTION APPARATUS

Our invention relates to ultrasonic inspection method and apparatus, and more particularly to a simple and economical ultrasonic apparatus which may be used to inspect hogs and cattle and the like, although the invention is also useful for various other inspection applications. The use of ultrasonic apparatus to painlessly and economically determine the fat, meat and muscle contents of portions of live animals, most frequently for selective breeding purposes, or to sort or classify animal carcasses, is well known and is achieving increasing popularity. Equipment commonly utilized for such purposes is shown, for example, in prior U.S. Pat. Nos. 3,603,303 and 3,722,263. While such equipment has proven to be extremely useful, it has had various limitations which have limited its use, and a primary object of the present invention is to overcome those limitations of such prior equipment.

The prior apparatus has used ultrasonic transducer guides, typically of arcuate shape and several feet long, which could be placed across the back or other desired sections of an animal, with motive means for driving the transducer along the guide as ultrasonic energy was transmitted into the animal and reflected ultrasonic energy was received. The reflected energy, or echoes, which represent density changes at various portions within the animal, were applied to intensity-modulate a line scan on a cathode ray tube, and as the transducer moved along the guide over successive portions of the animal, the line scan on the cathode ray tube was mechanically, optically or electrically moved relative to a photographic film frame to provide a pictorial representation of the density changes within the inspected portion of the animal.

Some serious limitations of such prior apparatus have been its limited portability, its consumption of substantial electrical power, and its great expense, which has been too great to allow its use by many animal breeders. The cathode ray tube displays used in such apparatus have been undesirably bulky, and their requirement for both high and low-voltage power supplies have undesirably contributed to their high cost, as well as ordinarily requiring that they be used near a power line. While it long has been theoretically possible to operate cathode ray tubes from batteries if suitable voltage conversion equipment and battery capacity was utilized, the cost, weight and bulk of necessary battery capacity and conversion apparatus having adequate power-handling capability has made battery operation of prior animal scanners impractical. The portability of the prior apparatus was also decreased and its expense considerably increased by the need for a photographic camera and mechanism to move the modulated scan line across the camera film. Great portability, with no need for a commercial power source is of great importance in the use of such equipment, since it is frequently necessary or desirable that animals be inspected under very adverse conditions in cattle pens or corrals, often in remote areas far from a commercial power line. In accordance with the principles of the present invention, the entire apparatus may be constructed so compactly as to be readily carried around the neck by one person, who can readily hold the transducer against the animal with one hand while adjusting the display with his other hand. Thus one important object of the invention is to provide improved ultrasonic animal inspection which is compact and readily portable.

Some features of the present invention are based in part on the fact that much information of interest concerning an animal considered for breeding purposes can be gleaned by visual observation of an appropriate indicator without the need for photographic recording. Indeed, persons lacking a scientific background or substantial experience in interpreting cathode ray tube displays find the display provided by the present invention easier to interpret. In addition to providing a more easily interpreted display and allowing one to avoid the expense and bulk of the optical and photographic components used in the prior apparatus, the present invention avoids the expense, bulk and power drain which attends use of a cathode ray tube. Thus a primary object of the present invention is to provide improved ultrasonic inspection method and apparatus useful for animal inspection which may be built simply and economically in compact and sound form, to use modest amounts of power and be capable of being powered over sustained periods of time, such as 8 hours, by a small re-chargeable battery, and an attendent object of the invention in accomplishing the aforementioned object, is to dispense with the need for a cathode ray tube in such equipment while providing a more readily interpretable display.

In prior art apparatus wherein ultrasonic echoes were recorded on photographic film, film sensitivity and incorporation of the cathode ray tube, lens and film plate within a light-tight enclosure allowed projection of cathode ray tube line scans having modest brightness. The provision of a display which may be observed directly by the operator is complicated by the fact that brightness of such a display must be orders of magnitude greater, if, for example, the apparatus is to be useful in daylight or sunlight, and the requirement of increased display brightness also tends to militate against the desiderata of low power consumption, compactness and ready portability.

While the prior art appartus provided cathode ray tube line scans which were intensity modulated in analog or continuous fashion by signals representing reflected ultrasonic energy, with each successive line scan changing as a transducer was moved over an animal in a predetermined path at a predetermined speed, and with each portion of the animal being scanned only once and with images of the successively different cathode ray tube line scans being recorded side by side on photographic film, the present invention instead contemplates use of an indicator comprising a linear array of light-emitting diodes which are controlled in digital fashion to be illuminated or not illuminated in accordance with whether their position along the array represents a depth within the animal where reflected ultrasonic energy falls below or exceeds a predetermined level, and provision of such method and apparatus are important objects of the invention.

The prior apparatus, like the present apparatus, was ordinarily made adjustable to inspect and display inspected areas of different sizes or depths by the use of several different scale factors. While persons having some experience with scientific instrumentation ordinarily can use the prior apparatus without error or confusion, the photographic displays provided by the prior apparatus have been difficult for some operators to easily interpret without error. In order to determine the thickness of a fat layer from a photograph made with the prior apparatus, the operator ordinarily had to measure the distance between two or more points having a given brightness on the photograph using a ruler or the like and keeping in mind the scale factor which had been used when the photograph was made. With the invention, the depths at which various density changes occur are indicated in inches (or centimeters, if desired) from one or more scales inscribed adjacent the linear array of lights, so that the operator may readily determine the thickness of fat layers and the like without manual measurement, and without confusion as to the scale factor used. Confusion as to which scale factor is used does not occur because which scale factor is being used is indicated by the position of a switch near the display while the display is being interpreted, so that no recollection of which scale factor was used previously is required. Thus one object of the present invention is to provide improved ultrasonic inspection apparatus in which the depths of density changes are indicated by a pattern of lights adjacent a numerical distance or depth scale.

With the prior apparatus it sometimes becomes apparent, after a photographic record is made using one scale, that better interpretation will result if a different scale were used. While the prior apparatus then may be switched to provide a second photograph on the preferred scale, such a procedure tends to waste film. Since the present invention requires no film, the operator can switch between different scale factors as desired without incurring such waste. Also, the inspection of some objects may be greatly facilitated if the receiver gain or detection sensitivity may be varied. In accordace with the invention, the sensitivity may be varied at will over a substantial range, without the film expense which would occur with the prior apparatus if a number of photographs were taken at a series of different sensitivities. Thus further objects of the present invention are to provide improved ultrasonic inspection method and apparatus in which scale factor changes and detection sensitivity changes may be readily made in the display at minimum expense.

The invention also contemplates provision and use of a continuously running or repetitive display wherein an apparently continuous display of reflected energy is observable by the operator as the transducer is positioned fixedly against the animal. This allows an operator to concentrate his observations in areas of particular interest, and to move back and forth across animal areas of special interest at any speed and direction he may find convenient, rather than being restricted to areas along a transducer guide in the manner of the prior apparatus.

In order to provide a display having a brightness readily interpretable by the operator, the present invention contemplates rapid and repetitive transmission of bursts of ultrasonic energy into the animal, broadly in the same manner as the prior apparatus, but storage of successive trains of signals representing ultrasonic echoes in a shift register which controls the array of light-emitting diodes (or "LEDs"), and a refreshing of the shift register contents by each of the successive trains of signals. Since clearing of previously stored register signals, transmission of an ultrasonic burst, and reception and storage of a train of echo signals may be accomplished in approximately a millisecond, the shift register contents may control the LED array for comparatively long times between successive signal trains, thereby providing a display having a high "duty-cycle" or "mark-space ratio", which is readily visible to the operator, and provision of such method and apparatus is a further important feature of the invention.

While digital or "on-off" control of the light-emitting diodes of an array inherently tends to illuminate each diode which represents an echo signal above a given amplitude in the same manner, more information can be obtained from the display if the relative magnitudes of various echoes can be determined, and a further object of some embodiments of the invention is to provide a digital display of received ultrasonic echoes from which the relative magnitudes of different echoes can be readily determined.

Other objects of the invention will in part be obvious and will in part appear hereinafter.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

For a fuller understanding of the nature and objects of the invention reference should be had to the following detailed description taken in connection with the accompanying drawings, in which:

FIG. 7a is a cross-section diagram through a hypothetical section of animal matter illustrating the locations of density changes, and FIG. 7b contains a plurality of diagrams illustrating various display patterns which may be produced by inspection of portions of the animal matter depicted in FIG. 7a.

Figure 8:
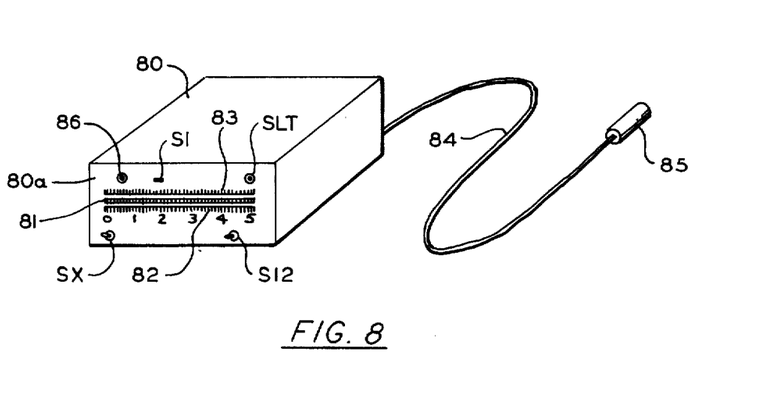
FIG. 8 is an isometric pictorial drawing illustrating one manner in which one embodiment of the invention may be physically packaged.

As illustrated in FIG. 8, the apparatus of the present invention may comprise a small box 80 having a volume of say 200 cubic inches which contains an ultrasonic transmitter, receiver, echo signal processing and display circuits, and associated power supply circuits, all powered by a small rechargeable battery carried within box 80. An end 80a of box 80 carries various switches and controls to be described, and has mounted thereon a linear array or row 81 of light-emitting diodes, such as 51 such diodes all preferably mounted abutting or closely adjacent each other. Scales are preferably inscribed on face 80a adjacent the row of LEDs, such as one scale 82 calibrated in portions of a total length of five inches and another scale 83 calibrated in portions of a total length of 10 inches. If desired, the scales can, of course, instead be calibrated in centimeters, and, in some embodiments a single scale, or more than two scales, may be provided. A length of coaxial cable 84, typically 3 or 4 feet, extends between box 80 and a hand-held probe 85 in which a piezoelectric ultrasonic crystal is mounted. Due to the small size and weight of box 80 and probe 85, it will be readily evident that both may be readily carried by one person, who may observe the LED display while pressing end of probe 85 against parts of an animal desired to be inspected. Box 80 may have one or more handles (not shown) mounted thereon. Alternatively, box 80 may be carried in a leather case (not shown) of the type frequency used for portable multimeters and like test instruments, and such a case may include a shoulder strap or belt clip to facilitate carrying. As well as an "on-off" switch S1, front panel 80a may carry a control knob 86 by means of which detection sensitivity may be varied, a switch SX to select whether the display is to cover a 5 inch or 10 inch depth, a switch S12 to select whether the display should include or ignore an outside layer of the object being inspected, and a "Test" pushbutton switch SLT for use in testing the operational condition of the display. With the unit within box 80 powered by turning on the on-off switch, pulses of electrical energy transmitted via cable 84 to the crystal carried within probe 85 causes bursts of ultrasonic energy to be transmitted into the animal, and ultrasonic echoes reflected back to the crystal by reason of density changes within the animal apply echo signals via the cable to signal processing circuits within box 80, eventually to operate the LED display. With the transducer positioned on the animal, the operator may observe the manner in which the display changes as sensitivity knob 86, and/or switched SX and S12 are varied. Various types of grease or oil are frequency applied to animal areas being inspected to improve ultrasonic coupling between the crystal and the animal.

Figure 7A:
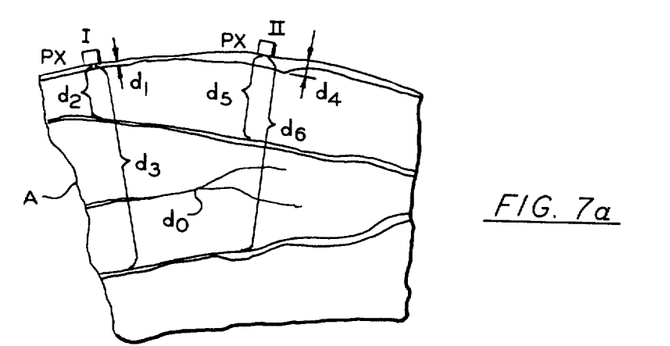
Figure 7B:
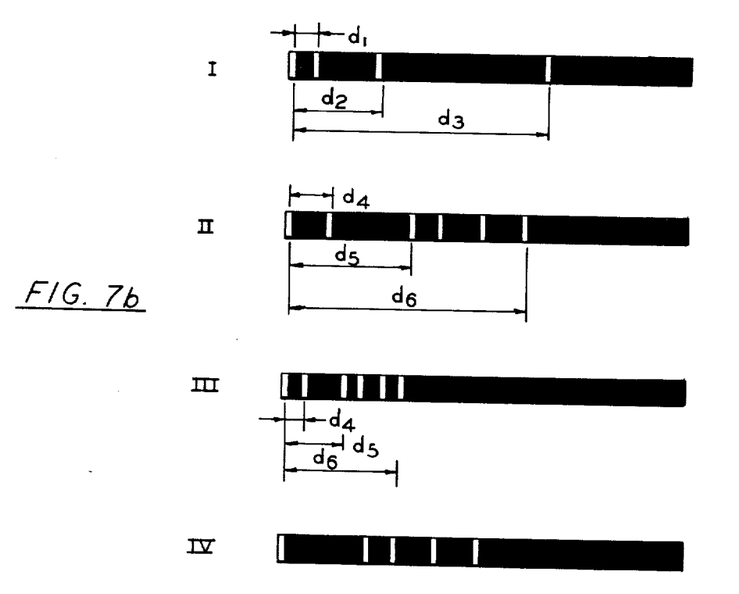

The general nature of the display provided by the preferred embodiment of the invention will become more evident by a consideration of the diagrams of FIGS. 7a and 7b, wherein a cross-section of animal is shown at A in FIG. 7a and an ultrasonic transducer crystal PX is shown positioned on the animal at two different positions labelled I and II. In position I ultrasonic energy will pass downwardly into the animal and substantial reflections of energy will occur at distances shown as $d_1$, $d_2$ and $d_3$ from the transducer where density changes at the interfaces of membranes, tendons, layers of fat or bone or the like exist. The reflection caused by the density change located distance $d_1$ from the animal surface will provide an echo signal from the transducer approximately at a time after transmission equal to $2d_1/s$, where s is the speed of sound in the animal matter located below the transducer to a depth $d_1$. Similarly, echoes from density changes located within the animal at distances $d_2$ and $d_3$ will provide echo signals at approximately times $2d_2/s$ and $2d_3/s$ after transmission of a burst of ultrasonic energy. In FIG. 7b the diagram at I illustrates the display which might be observed under such conditions. Four light portions represent four lighted LEDs in the linear array. The leftmost lighted LED represents the transmitter pulse, or an "echo" which occurs immediately upon transmission at the transducer-animal skin interface, and the distances of the other three lighted areas of the display from the left end of the display indicate the depths within the animal at which the density changes occur. A vein-like portion of animal matter labelled $d_o$ in FIG. 7a may be assumed to provide a reflection of limited magnitude compared to the others and does not result in a lighted LED. Under the conditions shown at II in FIG. 7a, continuations of the same animal portions which provided the three strong reflections of condition I similarly provide reflections at depths $d_4$, $d_5$ and $d_6$, to provide brightened display portions in the manner shown at II in FIG. 7b. The display at II in FIG. 7b also assumes, however, that the operator has increased the sensitivity of the device, and two additional reflections occurring from portions of veinlike piece $d_o$ are shown. As the operator moves the probe to different areas of the animal, different combinations of LEDs become lighted. By noting the distances of various lighted LEDs from the left end of the display, or by reading the position of a lighted LED against the one of the scales indicated by the then position of switch S12, the operator may determine the depth within the animal at which various density changes occur, thereby providing an insight into various animal characteristics. Assuming that the display at II in FIG. 7b represents that obtained using the smaller one of two scale factors, then III in FIG. 7b will represent the display obtained under the same conditions except that switch SX has been moved to select the larger scale factor. Each lighted portion representing an echo in the display at III is one-half the distance from the left end as the corresponding lighted portions of the display represented at II. In the displays at I, II and III in FIG. 7b the leftmost lighted portion represents the transmit pulse or the echo immediately received from the transducer-skin interface. As will be seen below, operation of switch S12 will provide a shifting of the display, so that the leftmost lighted LED will indicate the first actual echo from within the animal, and the transmit pulse of transducer-skin interface echo will not be displayed. Thus if the object portion which provided the pattern at II is inspected with switch S12 operated to one position, a display of the type shown at IV will be provided. The pattern at IV will be seen to correspond to that at II except that each lighted portion has been shifted distance $d_4$ to the left. The explanation of FIG. 7a is simplified in that it assumes the ultrasonic energy to travel in a narrow beam, while in fact it tends to disperse in a cone-like manner, so that some echo energy is returned from animal portions substantialy displaced from the transducer axes shown.

Figures 1, 2A, 2F:
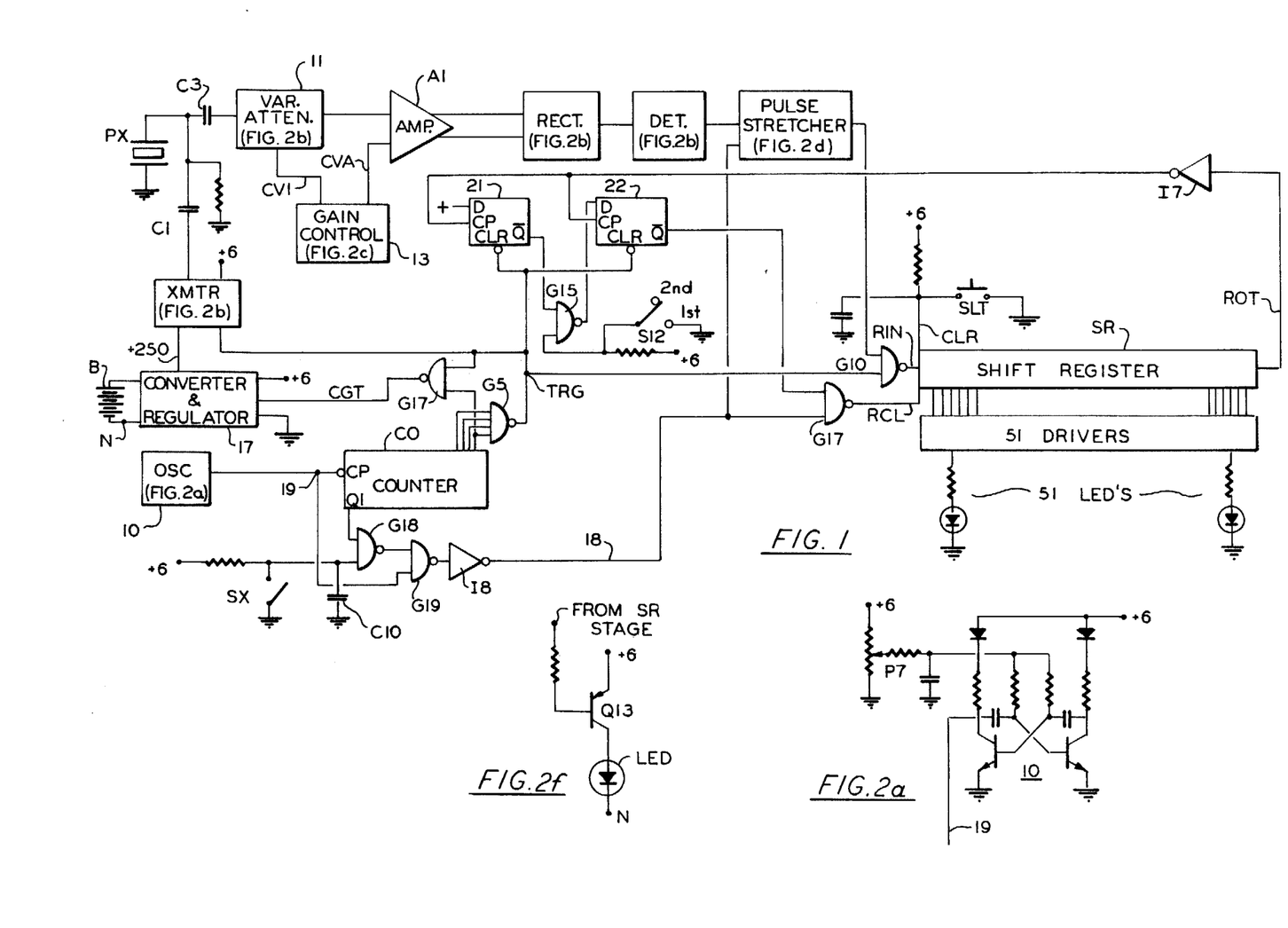
FIG. 1 is an electrical schematic diagram illustrating one exemplary embodiment of the invention.
FIGS. 2a–2f are electrical schematic diagrams illustrating portions of the device of FIG. 1 in greater detail, FIGS. 2d and 2e illustrating alternative forms of a pulse-stretcher circuit, only one or the other being needed for the device of FIG. 1.

A schematic diagram illustrating exemplary electronc circuitry which may be carried within box 80 is shown in FIG. 1. Basic timing for the system of FIG. 1 is provided by an oscillator shown in block form at 10, which may comprise a conventional free-running multivibrator providing output pulses on line 19 at a repetition rate of approximately 286 kilohertz, so that each cycle has a period of approximately 3.5 which whic is the time required for sound to travel approximately 0.2 inch (0.508 cm) in animal matter, and hence the round-trip time for energy to travel in both directions through animal matter having a depth or thickness of 0.1 inch. One simple form of such an oscillator is shown at 10 in FIG. 2a. the repetition rate of oscillator 10 is made adjustable over a limited frequency range for calibration purposes, potentiometer P7 being shown in FIG. 2a for that purpose. The multivibrator preferably is arranged to provide a square-wave output, i.e. one having high and low amplitude durations of approximately equal width although a square wave, as opposed to a rectangular wave is not necessary. Various frequencies, voltage values and other operational parameters mentioned herein for purposes of illustration are to be understood as being exemplary only. With one cycle of the oscillator frequency made equal to the roundtrip time for sound to travel 0.1 inch in animal matter, it will be seen that an echo occurring by reason of a density change located five inches within the animal will be received 50 oscillator cycles after a burst of ultrasonic energy is applied to the animal.

The negative transitions occurring at the 286 kilohertz repetition rate are applied via line 19 in FIG. 1 to the clock pulse input line of a twelve-bit binary counter CO, such as a commercially-available Type 14040, for example, thereby to repeatedly re-cycle counter CO through its 4096 count conditions, with a complete counting cycle thereby occurring every 14.34 milliseconds, or at a frequency of approximately 69.75 hertz. The four highest-order stage output lines of counter CO are shown connected to nand gate G5, thereby enabling gate G5 to lower line TRG during the last 256 counts of each complete counting cycle of counter CO, for a period of approximately 0.9 millisecond as the counter registers counts between 3840 and 4095 (decimal). Thus line TRG carries a waveform comprising successive cycles of the nature shown at TRG in FIG. 3.

Figures 2B, 2C:
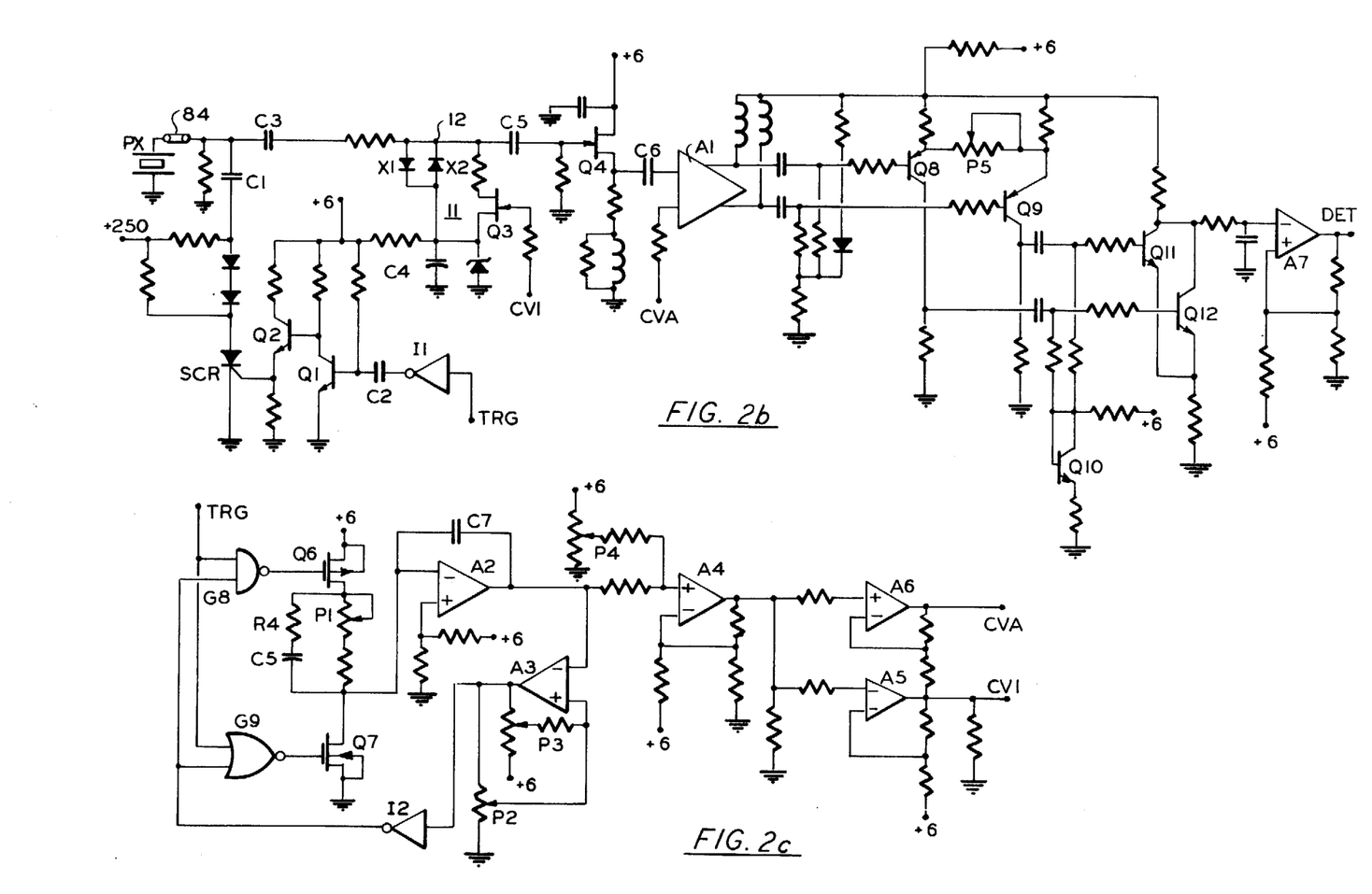
Figure 3:
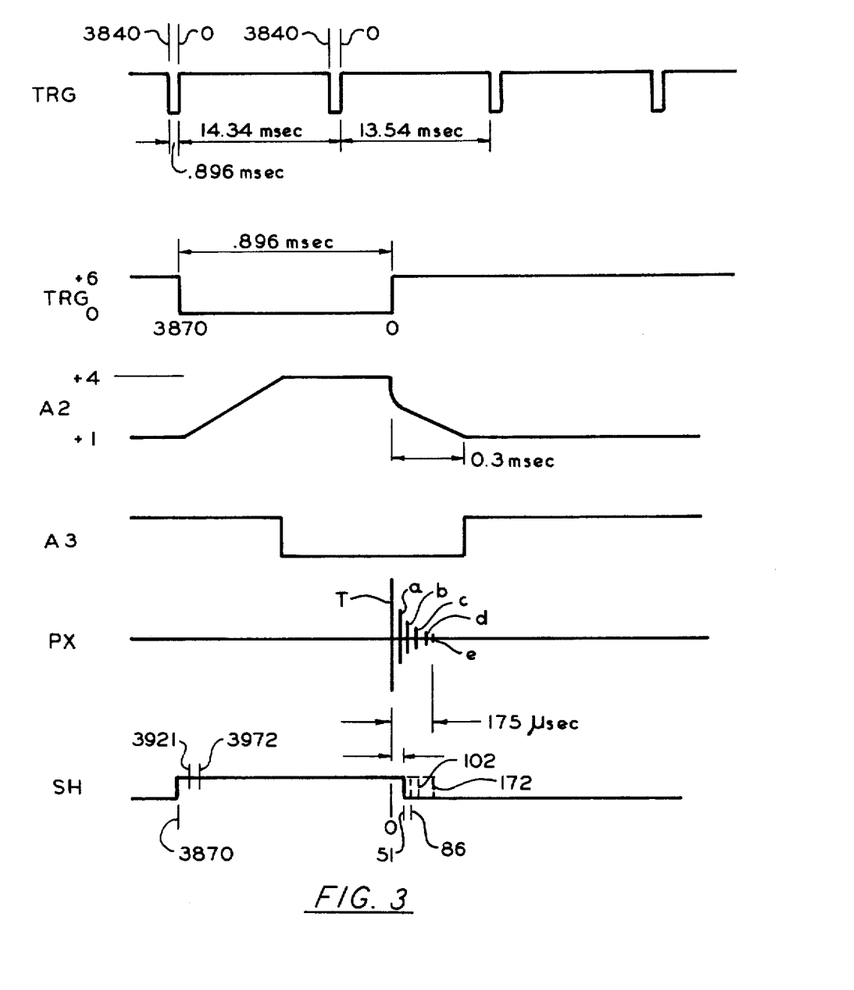
FIG. 3 is a plurality of waveforms useful in understanding operation of the device of FIG. 1.

As counter CO returns to a zero (or 4096) count condition, the rise of line TRG causes a momentary firing of a thyristor to apply a brief negative-going high-voltage pulse to ultrasonic piezoelectric crystal PX operated by a transmitter portion of the apparatus shown in block form in FIG. 1. As shown in more detail in FIG. 2b, the rise of line TRG drives the output of inverter I1 low, applying a negative pulse via capacitor C2 to turn off transistor Q1. The rise of the Q1 collector then turns on transistor Q2, thereby providing a positive pulse to the gate lead of thyristor SCR to turn on the latter. The negative pulse applied to crystal PX via capacitor C1 (and cable 84, FIG. 8) causes the crystal to oscillate or ring for several cycles at an ultrasonic frequency of the order of several megacycles, and thus ultrasonic energy is coupled from crystal PX within probe 85 to be transmitted to the animal or like object being inspected, and shortly thereafter one or several ultrasonic echoes representing density changes in the inspected object provide echo signals from crystal PX. A resistance shown shunting crystal PX insures that the ringing of the crystal decays rapidly in amplitude. The alternating voltage which occurs as the crystal oscillates, together with the voltage drop across series resistance between the high voltage supply and the SCR anode, causes the SCR to turn off after one-half cycle of crystal oscillation. Thyristor SCR must have a turnoff time no greater than one halfcycle of the crystal frequency to insure proper turnoff. The crystal will ring for plural cycles, with its oscillation amplitude decaying exponentially. In FIG. 3 at waveform PX the short burst or transmit pulse emitted by crystal PX is shown as a large spike at T, and five hypothetical echo pulses occurring shortly thereafter are shown at $a$ through $e$, equally spaced as if density changes were located at depths of 1, 2, 3, 4 and 5 inches respectively. With acoustical energy traveling 0.2 inch in 3.5 microseconds or 2 inches in 35 microseconds, it may be deduced that the five echoes shown would be received 35, 70, 105, 140 and 175 microseconds, respectively, after the transmit pulse. In practice the amplitudes of the echo bursts are far smaller in relation to that of the transmit pulse than is shown in FIG. 3.

A portion of each transmit burst, and the returning echo signals which follow shortly thereafter, are applied from crystal PX via capacitor C3 and a variable attenuator circuit 11 to a variable-gain amplifier A1. The variable attenuator 11 is provded so that the powerful transmit pulse will not saturate amplifier A1, and amplifier A1 is provided with a generally increasing gain during most of the time echo signals are being received, so that echoes representing more distant (i.e. deeper) density changes will have amplitudes generally comparable to those representing nearer density changes despite the greater attenuation resulting from their longer lengths of travel. As shown in FIG. 2b, pulses applied to or emanating from crystal PX are coupled via capacitor C3 to a variable attenuator which comprises FET transistor Q3. Diodes X1 and X2 form a bi-directional limiter, so that large amplitude pulses (e.g. greater than 0.7 volt) of either polarity will cause one diode or the other to conduct and shunt such pulses via capacitor C4 to ground, thereby limiting the voltage which occurs at terminal 12 when the transmit pulse occurs. The subsequently-occurring echo pulses have insufficient amplitude to cause either diode to conduct appreciably. Field effect transistor Q3 is controlled by a varying control voltage on line CVI to act as a variable shunt resistance, so that increasing amounts of the signal at terminal 12 are diverted to ground if the voltage on line CVI is rasised. The attenuated signal at terminal 12 is coupled through capacitor C5 to a source-follower stage comprising FET transistor Q4, and through capacitor C6 to a signal input terminal of variable-gain amplifier A1, which may comprise, for example, a Type MC1590 amplifier. The gain of amplifier A1 is controlled by the magnitude of a control voltage applied thereto on line CVA from a gain control circuit shown in block form at 13 in FIG. 1 and shown in detail in FIG. 2c.

Referring to FIG. 2c, when the TRG line goes positive at the zero count condition, nand gate G8 is enabled to turn on enhancement mode Pchannel mosfet transistor Q6, thereby applying a positive signal to the inverting input line of amplifier A2. The logic 1 signal on line TRG also provides a low output from nor gate G9, thereby turning off N-channel mosfet Q7. Feedback capacitor C7 connected from the A2 output terminal to the inverting input line causes the amplifier A2 circuit to intergrate its net input signal with respect to time. Slope adjustment potentiometer P1 adjusts the current applied to the inverting input terminal, and therefore the rate of decrease of the output voltage of integrator amplifier A2 from an initial value of approximately +4.0 volts at the zero count condition or transmit time to a final voltage of approximately 1.0 volt approximately 0.3 millisecond later, when a counter count of the order of 85 is registered. The output waveform of the integrator is shown at A2 in FIG. 3. A small RC lead circuit comprising resistor R4 and capacitor C5 causes the integrator output to decrease with a slope that is initially greater. The output voltage of integrator amplifier A2 is applied as shown in FIG. 2c to the inverting input line of switching amplifier A3, which is provided with two positive feedback circuits. The output waveform of amplifier A3 is shown at A3 in FIG. 3. When the A2 integrator output voltage begins to fall below +1.0 volt, the switching or comparator amplifier A3 outut voltage suddenly switches to a positive value, providing a low logic output from inverter 12 which disables nand gate G8 to turn off transistor Q6 and prevent further integration. The inverting input line of amplifier A2 then will be seen to be floating, and the integrator output will not change if the input current is zero. The integrator output voltage then remains at the 1.0 volt level until line TRG falls at the occurrence of the 3870 count condition. At that time, with the inverter 12 output still low, the fall of the TRG line causes the G9 nor gate output to rise, thereby turning on transistor Q7 to ground the inverting input line of integrator amplifier A2. With the inverting input line grounded, the negative current in the inverting input line then causes the integrator output to ramp upwardly to the upper limit value of +4.0 volt, thereby insuring that attenuator 11 will be controlled to provide maximum attenuation and that amplifier A1 will be controlled to provide a minimum gain shortly thereafter when the next transmit pulse occurs. The magnitude of the voltage applied to the non-inverting input line and the value of the integrator feedback capacitor C7 are selected so that the integrator output will reach its maximum value (of approximately 4.0 volts) roughly midway in the interval during which the TRG line is low. When the integrator output reaches a value of +4.0 volts, the output voltage of comparator amplifier A3 suddenly swings to a logic zero level, providing a logic 1 signal from inverter 12 and a logic zero signal from nor gate G9 to turn off mosfet transistor Q7, thereby releasing the inverting input line of amplifier A2 and halting upward integration. The two integrator output levels at which amplifier A3 switches may be adjusted by means of lower limit potentiometer P2 and high limit potentiometer P3. The 1.0 volt and 4.0 volt levels mentioned are, of course, exemplary only, and the amount which the gain is automatically changed with time as echoes are being received is in some respects a matter of choice. In one typical application where echoes representing quite deep density changes were desired to be displayed, the gain was automatically increased by about 80$dB$, while in another typical application where deep density changes were regarded to be less important, the gain was automatically increased by about 30 $dB$. It is possible to mount potentiometers P2 and P3 to make then accessible for adjustment by the operator, for use of the invention under widely varying conditions, but ordinarily we prefer that they not be accessible.

The output of the integrator circuit is applied to summing amplifier A4 together with a bias signal from gain adjustment potentiometer P4, which may be adjusted by means of knob 86 (FIG. 8) carried on the face of the instrument. The output of amplifier A4 is applied as shown in FIG. 2c to amplifier A5 and A6, each of which is provided with a gain consonant with the variable gain characteristic of the device which it drives, the output of amplifier A5 on line CVI driving the gate lead of FET transistor Q3 of the variable attenuator 11 (FIG. 2b) and the output of amplifier A6 on line CVA driving the gain control input line of variable-gain amplifier A1. The more positive the signal on line CVI, the greater the attenuation of attenuator 11, and the more positive the signal on line CVA, the less is the gain of amplifier A1. Thus as the integrator circuit output signal ramps downwardly for approximately 0.3 millisecond immediately after line TRG rises and the crystal stal PX is energized with a transmit pulse, the attenuation of attenuator circuit 11 decreases, preferably linearly in $dB$, or exponentially, from a maximum value to a minimum value, while the gain of amplifier A1 simultaneously increases from a minimum value to a maximum value, as echoes having increasingly longer paths of travel are received.

Amplifier A1 is shown as providing a pair of pushpull or complementary output signals. The output signals from amplifier A1 are applied to a full-wave rectifying or asolute value circuit 15 shown in detail in FIG. 2b, being bandpass filtered by conventional filtering shown at the output of amplifier A1. The two filtered output signals are applied to transistor Q8 and Q9, respectively, these two transistors serving to amplify the filtered signals. Inasmuch as the two signals are of opposite sense, the resistance path interconnecting the emitters of transistors Q8 and Q9 provides negative feedback, and adjustment of potentiometer P5 in that path also allows the gain of each signal to be adjusted. Transistor Q10 acts as a diode which, together with the resistive divider shown, accurately biases transistors Q11 and Q12 just at cutoff, for class B operation. Thus an input pulse of one sense applied to amplifier A1 causes transistor Q11 to conduct, applying a negative pulse to comparator A7, while an input pulse of opposite sense applied to amplifier A1 instead causes transistor Q12 to conduct, similarly applying a a negative pulse to comparator A7. The input signals to comparator A7 are applied with some low-pass filtering to eliminate high frequency ripple. Comparator A7 is provided with high gain, and hence the A7 output line labelled DET swings to a high or logic 1 level when the transmit pulse occurs and thereafter whenever an echo signal is being detected, and instead swings to a low or logic zero level when no echo is being received. The comparator A7 may be provided with positive feedback as shown to cause it to switch with a measure of hysteresis, but such use of positive feedback is not necessary. By adjustment of gain potentiometer P4, it will be seen that the operator may vary the echo magnitude required to provide a logic 1 signal on line DET, thereby varying the sensitivity of detection. With the transducer PX applied to a given portion of the animal, the gain may be gradually varied over a wide range to provide a varying display as successive display cycles occur.

Figure 2D:
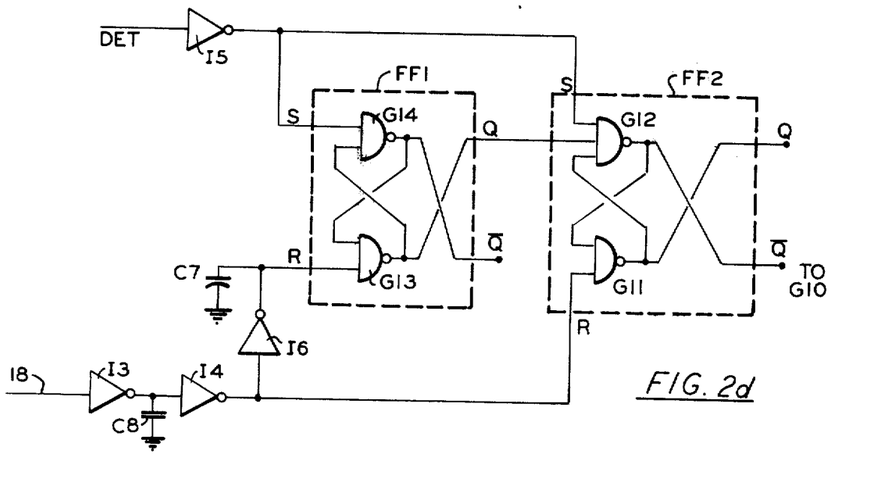
Figure 2E:
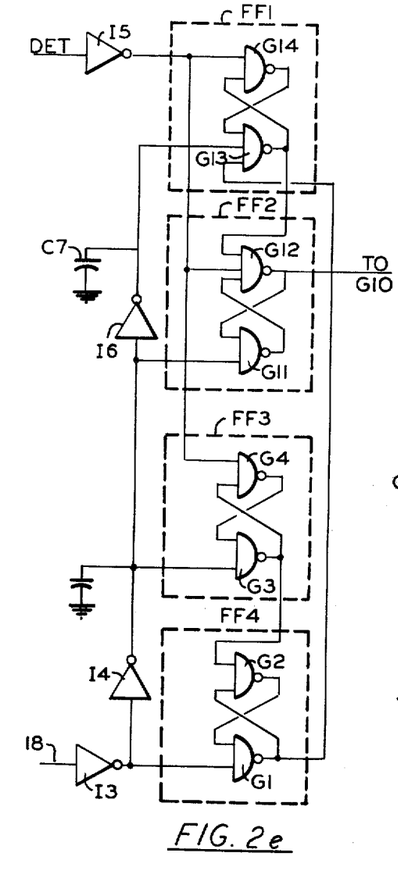

The logic signals on line DET indicating the presence or absence of echoes are applied to pulse stretcher means shown in detail in FIG. 2d, or alternatively, an improved form of pulse stretcher shown in FIG. 2e may be used. Echoes may be received at any time between successive negative clock transitions, they may or may not bridge a negative clock transition, and a given echo may not have a duration as long as the interval between successive clock transitions. In order than an echo be registered even if it does not persist until the next clock transition, the circuit of FIG. 2d may be utilized to store each logic signal representing an echo until the next negative clock transition.

A simplified form of pulse stretcher shown in FIG. 2d comprises a first RS flip-flop FF1 composed of cross-coupled nand gates G13 and G14, and a second RS flip-flop FF2 composed of gates G11 and G12. A complete clock period will be understood to comprise a pair of half-period intervals, during one of which clock line 18 is high and during the other of which line 18 is low. Shift register SR (FIG. 1) is shifted at the time of negative-going transitions of line 18, when the output of gate G17 (FIG. 1) drives the register shift line RCL positive.

When no echoes are being received, so that line DET is low, inverter 15 provides a logic 1 signal to the set input lines of each flip-flop. At the beginning of a half-period interval when clock line 18 goes high, the low input applied to gate G13 via inverter 16 makes the G13 output high, and the G13 output, together with the inverter 15 output, makes the gate G14 output low, so that flip-flop FF1 is set, with gate G13 providing logic 1 on the Q output line FF1. During the succeeding half-period intervals when clock line 18 goes low, the high input from inverter 16 cannot enable gate G13 because of the low input from gate G14, and hence flip-flop FF1 remains set. Thus in the absence of receipt of an echo flip-flop FF1 remains set. During a half period interval when clock line 18 is low, the output of gate G11 must be high, so that gate G12 is enabled, and thus in the absence of receipt of an echo, flip-flop FF2 is also set, with gate G11 providing logic 1 on the Q output line of flip-flop FF2. Hence unless and until receipt fan echo signal raises line DET, both flip-flops remain set, gate G12 provides a low signal on the Q̄ output line of flip-flop FF2, maintaining gate G10 (FIG. 1) disabled, so that each raising of line RCL stores a logic 1 signal in shift register SR.

Next assume that an echo pulse is momentarily received during a half clock period while line 18 is low, so that the inverter 15 output momentarily goes low. The fall of the inverter 15 output will disable gate G14 to immediately clear flip-flop FF1, and the fall of the G13 output will keep FF1 cleared after disappearance of the momentary echo pulse. The fall of the inverter 15 output will also momentarily disable gate G12 while the echo pulse persists, but the low output from inverter 14 will maintain gate G11 disabled, so that flip-flop FF2 will still be set after disappearance of the echo pulse. Then later, as clock line 18 rises at the end of that half period, the low output from gate G13 resulting from the prior clearing of FF1 by the echo pulse will be disabling gate G12, so that the rise of clock line 18 enables gate G11 to clear flip-flop FF2. The rise of clock line 18 also disables gate G13 via inverter 16 to return flip-flop FF1 to the set condition. Capacitor C7 slightly delays the setting of flip-flop FF1 to insure that FF2 will be properly cleared before FF1 is again set. Then flip-flop FF2 remains cleared throughout the half period while line 18 is high, so that gate G12 enables gate G10 to store a zero in the shift register at the end of that half period, and the fall of line 18 then sets flip-flop FF2, with a small delay being provided by capacitor C8 to insure that the shift register has stored the zero before FF2 is again set. Thus receipt of an echo signal while line 18 is low results in an immediate clearing of FF1, a transfer of that clearing to FF2 when clock line 18 goes high, and then storage of a logic zero in the shift register when line 18 next goes low.

If an echo pulse is instead received while line 18 is high, the low input from inverter 16 to gate G13 prevents flip-flop FF1 from being cleared, but flip-flop FF2 will be cleared, and then at the end of that half period as clock line 18 goes low, a zero will be stored in a register SR and flip-flop FF2 then switched again to a set condition, in the same manner as previously described. Thus it will be seen that a logic zero will be stored in the register if a momentary echo pulse occurred during either half of the preceding complete clock pulse period. If an echo pulse has a duration such that is sufficiently bridges in time a negative clock transition on line 18, logic zeroes will be stored in two successive stages of the shift register. Improved resolution may be provided in the display by use, in lieu of the pulse stretcher of FIG. 2d, of a preferred form of pulse stretcher shown in FIG. 2e, which prevents a single echo pulse on line DET from storing logic zerors in two successive stages.

In FIG. 2e parts generally similar in function to those of FIG. 2d are given similar designations. The pairs of gates G11, G12 and G13, G14 form RS flip-flops as in FIG. 2d, but gate G13 in FIG. 2e now has three inputs. A flip-flop FF3 formed by gates G3 and G4 is cleared upon the occurrence of an echo during a clock half-period when clock line 18 is high, in a manner similar to the G11-G12 flip-flop FF2, bur flip-flop FF3 is not connected to be controlled by flip-flop FF1. Instead, an output from the G3-G4 flip-flop FF3 controls a fourth flip-flop FF4 formed by gates G1 and G2. When line 18 next goes low, the clear state of flip-flop FF3 is transferred to flip-flop FF4. An output from flip-flop FF4 is applied to flip-flop FF1, and hence if the echo signal received just prior to the clock negative transition persists into the next clock half-period, it will not be redetected during the next half-period and registered a second time. Thus the pulse stretcher circuit of FIG. 2e cancels detection during the clock half-period following the clock transition time at which the register is shifted if an echo pulse was detected during the immediately-preceding clock half-period, and hence an echo which merely bridges a register shifting instant will not cause logic zeroes to be stored in two adjacent stages of the shift register.

During each period of up to approximately 350 μs which begins with each transmit pulse, the occurrence of the transmit pulse and then the occurrences of returning echoes are registered (as zeroes) in various stages of the shift register SR and shifted toward the output end of the register. The zero representing the transmit pulse will be shifted into the last stage of the register approximately 51/285,714 or 178 μs after the transmit pulse with the frequencies heretofore mentioned, if switch SS is positioned to connect to the 51st stage (and switch SX is transferred from the position shown in FIG. 2a). When that logic zero siganal arrives at the last stage of the shift register, inverter 17 provides a logic 1 signal to the clock input lines of each of a pair of Type D flip-flops 21 and 22. If prior to that time switch S12 has been transferred from the position shown in FIG. 1, so as to disable gate G15, the logic 1 signal from inverter 17 will immediately set flip-flop 21 and 22, disabling gate G17 and interrupting the application of shift pulses to shift register SR, so that the last stage of the shift register will indicate the transmit pulse, providing a display of the general nature shown at II in FIG. 7b. Conversely, if switch S12 is positioned as shown in FIG. 1, so that gate G15 were enabled, the logic 1 signal occurring from inverter 17 when the zero representing the transmit pulse is shifted to the last stage of the shift register will set flip-flop 21 but not flip-flop 22. However, when the logic zero signal representing the first echo received after the transmit pulse reaches the last stage of the shift register, the logic 1 signal from inverter 17 will set flip-flop 22 since flip-flop 21 being already set provides a logic one to the D input of flip-flop 22, thus disabling gate G17 and interrupting the application of shift pulses to the shift register, and then the output end of the shift register, i.e. the LED driven by the last stage of the register, will indicate the presence of the first echo, thereby providing a display of the general nature shown at IV in FIG. 7b. If, by way of example, the first detected echo occurred from a density change approximately 0.6 inches from the transducer, so that it would be detected approximately 21 microseconds after the transmit pulse, shifting of the register would be stopped 21 + 178 or 199 microseconds after the transmit pulse. It should now be apparent that by interconnection of flip-flops in generally the manner shown for those at 21 and 22, and with use of a multi-position switch in lieu of switch S12, the apparatus may be arranged, if desired, to display the 3rd, 4th or other received echo in the endmost stage and to ignore earlier received echoes. However, as will be explained below, it is not necessary that register shifting be terminated by sensing the emergence of a given logic signal from the shift register.

It was made apparent above that during the receiving interval following each transmit pulse, the received echo signals are shifted along the shift register at a speed dependent upon the repetition rate of the clock signals on line 18. In FIG. 1 gate G18 is connected to receive the first stage output signal of counter CO. If switch SX is transferred from the position shown, to continuously disable gate G18, each negative input pulse to counter CO on line 19 will cause gate G19 to be disabled, thereby providing a negative transition on line 18, so that the shift register shift rate will equal the counter counting rate and 178 microseconds will be required to shift a given logic signal the entire length of the 51-stage register. Conversely, if switch SX is in the position shown, so that gate G18 is conditionally enabled by the constant logic 1 signal applied to one of its input lines, gate G18 will be enabled and gate G19 disabled only during the negative transitions of line 19 following alternate count conditions, so that the shift register shifting rate will be one-half the counter counting rate, and then approximately 356 microseconds will be required to shift a given logic signal the length of the shift register. Decreasing or increasing the register shift rate will be seen to decrease or increase respectively the number of register stages among which echo signals detected during a given time interval are stored, thereby decreasing or increasing respectively the resolution of the final LED display, and increasing or decreasing respectively the depth of the inspected object over which density variations are indicated. It should become apparent at this point that by minor revision of the frequency division circuit in between lines 19 and 18 one may increase or decrease the resolution and depth indication displayed by factors other than two. For example, use of the counter second stage output in lieu of that of the first stage would cause operation of switch SX to vary resolution and displayed depth by a factor of four. Further, it is not necessary that the shifting rate be equal to or less than the counter rate. It will be apparent that the oscillator 10 output on line 19 could be divided by one or more cascaded flip-flops (not shown) to provide the counter CO drive signal, but applied directly to line 18, so that the shifting rate would be greater than the counter rate by some desired multiple.

During the 256 counts or 896 microsecond period preceding the transmit pulse while line TRG is low, gate G10 will be seen to be disabled, so that a logic 1 signal is carried on the shift register input line RIN. During that same time interval flip-flop 22 is held cleared by line TRG so as to enable gate G17 and hence a continuous train of logic 1 signals wil be shifted into the register. Any zeroes theretofore contained in the register will be shifted out of the last stage of the register and lost, and with flip-flop 22 held cleared by the TRG line, the application of a logic zero to inverter 17 does not interrupt shifting. With 51 register stages, it will be seen that all zeroes will be shifted from the register no later than the 3870 + 51 or 3921 count condition, or the 3870 + 102 or 3972 count condition, depending upon the position of switch SX. Thus by the time the TRG line rises to provide the transmit pulse, it is assured that the register contains all logic 1 signals and hence all LEDs of the display will be turned off. After the transmit pulse, register shifting continues, as previously mentioned, until the transmit pulse (or the first echo after the transmit pulse, depending upon the position of switch S12) reaches the last stage of the register. In FIG. 3b the waveform SH indicates the time during which shifting occurs. With shifting beginning at a counter count of 3870, all zeroes are removed from the register by the time a count of 3921 or 3972 is reached, depending upon the position of switch SX. All LEDs then remain unlighted until the tranmit pulse occurs at a zero count. The drop of line SH at a count of 51 assumes switches S12 and SX to be opposite to the position shown in FIG. 1, so that emergence of the transmit "echo" from the register operates flip-flop 22 to terminate shifting. With switch S12 instead in the position shown, shifting is terminated by echo a, assumed to occur 35 counts later. With switch SX in the position shown, shifting is terminated at a count of 102 or a count of 172, depending upon the position of switch S12.

The filling of the register with logic 1 signals for a brief interval after the lowering of the TRG line, the presence then of all unlighted LEDs until the transmit pulse, and then the energization and de-energization of the LEDs of the display in a rapidly-changing pattern would tend to be meaningless to the operator were he capable of observing them. However, the operator cannot possibly observe illumination or non-illumination of an LED which lasts less than one millisecond, and indeed cannot ordinarily notice any flicker as the display is refreshed at approximately a 70 hertz rate. With illumination of the LEDs cutoff or changing during a period of approximately 428 counts or 1490 microseconds (as the counter counts from 3870 to 172) and the display then remaining unchanged for a period of approximately 3668 counts or 12,838 microseconds (as the counter counts from 172 to 3870), the duty cycle of the display will be seen to exceed 89%. With the transducer positioned at a fixed position on the animal, the observed display appears as a steady pattern of illuminated and unilluminated elemental areas.

The shift register may comprise a group of cascaded integrated circuit shift registers, such as commercially-available Type 74C164, for example. The preferred embodiment being described in detail utilized seven cascaded 8-stage registers to provide 56 available stages, with output signals from 51 stages of the shift register individually connected through respective driver transistors to illuminate respective ones of the LEDs, the connection of one such driver transistor being shown in FIG. 2f. If the stages are numbered left to right as 1 through 56 in FIG. 1, the LEDs are ordinarily connected to the output lines of stages 1 through 51.

Figure 6B:
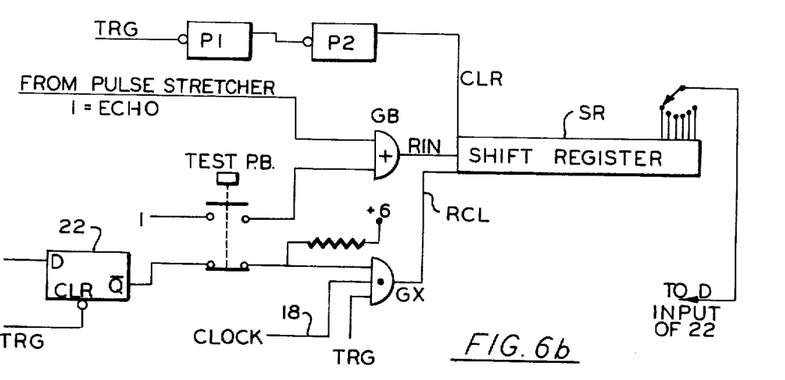

While FIG. 1 illustrates one arrangement for terminating shifting of the register, several alternative arrangements may be used. For example, rather than using the emergence of the stored transmit pulse or an echo pulse from the shift register to terminate shifting, gates (not shown) may be connected to counter CO to set flip-flop 22 to terminate register shifting at one or more particular counts, such as 51 and 102, for example. As a second example, a separate counter receiving the same input pulses as counter CO but having a lesser count capacity, such as approximately 51 or 102 counts, may be used to terminate shifting. Rather than using an additional flip-flop and switch S12 to prevent the transmit pulse from being displayed as an echo, the register output signal applied to inverter I7 may be taken from a register stage beyond those which drive the LEDs. For example, if the shift register is provided with 56 stages, with LEDs connected to be driven by only the first 51 stages, and if the inverter I7 output is connected to set flip-flop 22 (with switch S12, flip-flop 21 and gate G15 omitted and a constant logic 1 applied to the D input of flip-flop 22), deriving the inverter I7 input from any one of stages 52 to 56 of the register would insure that the transmit pulse would not illuminate the first LED, i.e. the LED driven by the 51 stage of the register. If a selector switch (not shown) is provided to select the output of any selected one of stages 52 to 56 to inverter 17, it will be seen that moving the switch to select earlier or later ones of those stages will serve to shift the pattern of illuminated LEDs in one direction or the other along the row of LEDs. Use of such a technique is shown in FIG. 6b in connection with a modified embodiment, but the technique can, if desired, be used in an embodiment otherwise corresponding to FIG. 1.

In the above explanation wherein it has been stated that logic zeroes (rather than logic ones) are stored in the shift register to represent echoes, it is recognized that whether the state of a shift register stage is deemed logic 1 or instead logic 0 is sometimes a mere matter of arbitrary terminology or terminal labelling. The preferred embodiment described above stores logic zeroes to represent echoes in the sense that logic zero is assumed to be the state to which all stages of the register will be switched by actuation of a conventional register "clear" line. Temporary actuation of "Test" pushbutton switch SLT to lower the register clear line causes all of the LEDs of the display to be illuminated, affording the operator a quick and easy way of checking to see that all LEDs are functioning properly. Also, since the LEDs draw considerably more current than the remaining portions of the apparatus, depression of the test pushbutton also may be used to check the condition of the battery, as will be better understood as the description proceeds.

Figures 4, 6A:
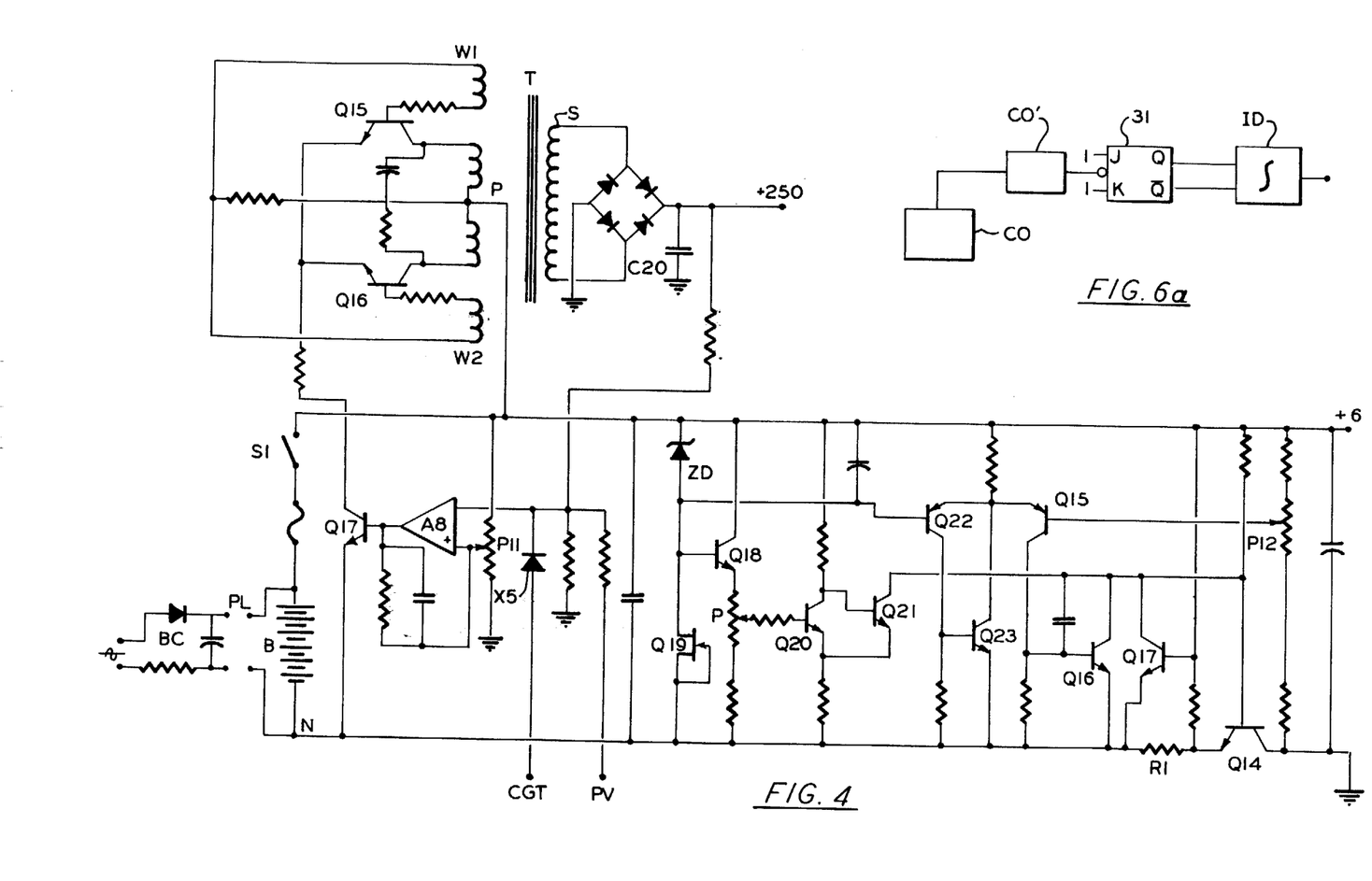
FIG. 4 is an electrical schematic diagram illustrating one form of power supply apparatus which may be used with the apparatus of FIG. 1.
FIGS. 5, 6a and 6b illustrate various modifications which may be made in the device of FIGS. 1–4.

The power supply apparatus shown as a simple block at 17 in FIG. 1 is shown in greater detail in FIG. 4. The terminals of battery B are routed to a plug PL for connection to a simple battery charger shown at BC. With on-off switch S1 closed, battery current flows to the centertap of the primary winding P of a small toroidal transformer T, and thence through one half or the other of winding P and the collector-emitter circuit of an associated transistor Q15 or Q16 to the negative battery terminal, through control transistor Q17. Current flow in primary winding P induces voltages in feedback windings W1 and W2, alternately driving transistors Q15 and Q16 between cutoff and saturation conditions, so that the current in winding P oscillates and induces a voltage having a peak value of the order of 300 volts in secondary winding S. The secondary voltage is full-wave rectified, by means of the rectifier bridge shown, and filtered by means of a small caapacitor C20, thereby to provide the high-voltage of +250 volts required to pulse the piezo-electric crystal PX. A small fraction of the high voltage sensed by a simple voltage divider is applied to comparator A8 to be compared with a fraction of the regulated 6-volt appearing on the wiper arm of potentiometer P11. When the high voltage across capacitor C20 is less than a desired value, comparator A8 turns on transistor Q17 to allow the primary winding circuits to oscillate and increase the high voltage, and when the high voltage reaches a value determined by the adjustment of potentiometer P11, comparator amplifier A8 turns off transistor Q17 until the high voltage again falls below the desired value. Because the oscillations of the DC-to-DC converter shown can generate stray noise which is substantial in magnitude compared to the echo signals, means shown as comprising an input from line CGT through dioxe X5 to comparator A8 serves to switch amplifier A8 and interrupt operation of the DC-to-DC converter during each interval while echoes are being received, thereby obviating the problem of converter noise during those intervals. As shown in FIG. 1, the TRG line, which is high during the counts from zero to 3870 and the output of the last stage of counter, which is high during the counts 2048 to 4096 of a complete counter cycle are applied to gate G17, thereby lowering line CGT during the time interval between counts 2049 and 3870, but otherwise holding line CGT high to disable the DC-to-DC converter. Thus the converter operation does not generate noise during the time interval following the transmit pulse at the zero count time during which echoes are being received.

A regulated power supply also shown in FIG. 4 provides a regulated 6-volt source to operate the amplifying and logic circuits of FIG. 1. The LEDs of the display are driven directly from the battery terminals, i.e. without regulation each LED being connected directly to battery terminal N, thereby by-passing regulator transistor Q14. Series transistor Q14 comprises the main control element of the regulator and zener diode ZD comprises the reference voltage element. Transistor Q19 is connected to apply a constant current to diode ZD, to provide a constant voltage across that diode over a wide range of battery voltage variation. The reference voltage across diode ZD is applied, via a low-pass filter, to one input line of a differential amplifier, while a sample of the output voltage is applied from the arm of potentiometer P12 to the other input line of the differential amplifier. Transistor Q22 and Q23 connected in bootstrap emitter follower configuration form one side of the differential amplifier, while transistors Q15 and Q16 connected in a similar configuration form the other side. Thus the differential amplifier compares the sample of the existing output voltage from potentiometer P12 with the zener-derived reference voltage. If the regulated outut voltage at the +6 terminal tends to decrease, the decreased base drive tends to decrease the current through transistor Q15, in turn decreasing Q16 current. Since Q16 diverts base current from series transistor Q14, decreased current through Q16 causes increased current through transistor Q14, and restoration of the desired output voltage. Converse operation which occurs upon an increase in the +6 output voltage will be evident without further explanation. If too much current tends to be drawn from the power supply, the increased voltage drop across series resistor R1 will be seen to tend to turn on transistor Q17, diverting base current from series transistor Q14, and thereby limiting the current which can be drawn from the supply.

It is desirable that operation of the apparatus be terminated if the battery charge becomes too low, both to avoid unreliable inspection operations and to avoid battery damage. The emitter of emitter follower transistor Q18 rises and falls the same amount as the battery voltage. A decrease in battery voltage tends to turn off Q18 and thereby turn off transistor Q20, and a sufficient decrease in battery voltage will turn on transistor Q21 very hard, diverting substantially all the base current from series transistor Q14 and thereby cutting off the +6 volt supply, so that operation cannot continue to further discharge the battery. The battery voltage at which such shutdown will occur may be adjusted by means of potentiometer P.

Because the illumination of the entire LED display requires much more current than that required by the amplifier and logic circuits, operation of the Test switch ( to close contacts SLT in FIG. 1) represents a battery drain considerably greater than that encountered during normal operation of the apparatus. If the battery is sufficiently charged, depression of the Test pushbutton will clear the shift register, and all of the LEDs of the display will become lighted. If the battery is not sufficiently charged, the substantial drain imposed on the battery by the LEDs will lower the battery voltage to a lowered value, causing shutdown of the regulated 6-volt supply in the manner previously explained. De-energization of the shift register upon shutdown cuts off each of the driver transistors feeding the LEDs, thereby extinguishing the display, cutting off battery drain. Hence depression of the Test button will cause the entire LED display to go off if the battery is not adequately charged, thereby warning the operator of the battery condition.

Figure 5:
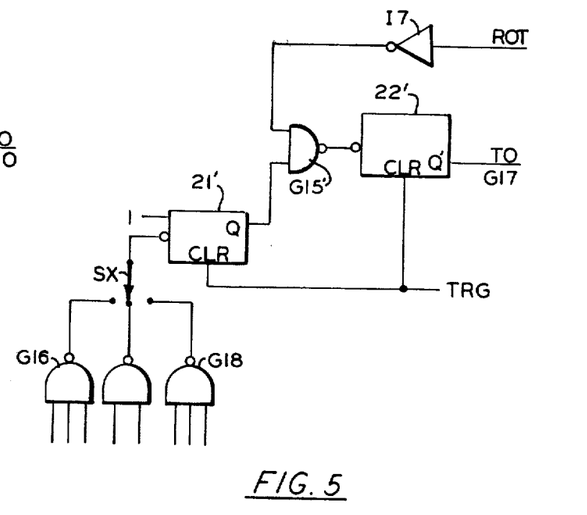

It was explained above in connection with FIG. 1 that operation of switch S12 allows the display to ignore the transmit pulse and to indicate the first density change below the surface of the inspected object, plus each further or deeper density change, over a limited depth, of course. In certain applications it may be deemed desirable to ignore one or more echoes occurring at less than a given depth, so that echoes occurring from deeper density changes may be displayed with greater resolution, for example. In a modification illustrated in FIG. 5, register shifting is terminated by the first echo pulse detected after a predetermined interval following the transmit pulse, and at that time the logic signals resulting from any earlier-received echoes will have been shifted out of the register. Three gates shown at G16 to G18 are assumed to receive signals from different selected groups of output lines from stages of counter CO, and selector switch SX' allows the low gate output signal which occurs upon a predetermined count condition to set flip-flop 21' and thereby conditionally enable gate G15', so that a logic 1 echo-indicating signal occurring thereafter from inverter 17 will set flip-flop 22' and terminate shifting.

As will be understood from the preceding description of the FIG. 1 device, each LED is lighted or not lighted during the display interval in dependence upon whether reflected ultrasonic energy was above or below a given threshold level during the brief receiving period initiated at each transmit pulse time. Thus if the transducer is held in fixed position relative to the animal, and density changes do not occur within the animal, the observed display will consist of certain LEDs seemingly continuously lighted to represent depth portions of substantial density change, but all lighted LEDs will have the same apparent brightness, irrespective of whether the echoes which caused their illumination barely exceeded the threshold level or greatly exceeded the threshold level. For some applications it is deemed desirable to display the relative magnitudes of substantial density changes. In accordance with a modification of the invention illustrated in FIG. 6a, the gain of the ultrasonic amplifying channel is swept or varied over a predetermined range during a time interval which embraces a plurality of transmit pulses and reception intervals, such as six such intervals, for example. Echoes providing very strong signals will provide logic signals to light their respective LEDs during each of those intervals, while echoes of progressively less amplitude will provide logic signals to light their respective LEDs during fewer of those intervals. Thus strong echoes will provide greater average illumination of their respective LEDs, so that the relative strengths of the echoes may be readily observed. in FIG. 6a, the last stage of counter CO feeds a further counter CO' which counts a selected number of transmit pulses, toggling flip-flop 31 after each group of transmit pulses, and switching flip-flop 31 between its two states causes a conventional analog integrator ID to integrate successively in opposite directions. The output voltage of integrator ID may be connected to vary the gain (or attenuation) in a variety of different ways, by controlling amplifier A1, or the Q3 attenuator, for example, by merely combining the integrator output with the CVA or CVI signal, or, if desired, the integrator output may be arranged to vary the detector thresholds, by connection of the integrator output through a resistor to the non-inverting input line of comparator A7, for example. It is also posible to vary the transmitter output pulse magnitude instead of the receiver gain. For example, the output of integrator ID of FIG. 6a could be applied bo terminal PV in FIG. 4, thereby to vary the high voltage provided by the high voltage power supply and hence cyclically vary the magnitude of transmitted output pulses.

In a modified arrangement partially shown in FIG. 6b, the TRG signal is assumed to be developed in the same manner as in FIG. 1. However, logic 1s are stored in the register to indicate echoes, via or gate GB, it being assumed that logic 1 output signals from the pulse stretcher represent echoes. During operation, the fall of each TRG pulse triggers a pair of cascaded one-shots P1 and P2, timed so that P2 clears the shift register shortly before, such as a microsecond or two before, each transmit pulse. The exit of the logic 1 transmit pulse from a selected stage near the end of the shift register sets flip-flop 22 to stop shifting, in a manner similar to FIG. 1 (except inverter 17 of FIG. 1 is omitted). The low $\overline{Q}$ ouput of flip-flop 22 overrides the constant logic 1 signal applied to and gate GX when flip-flop 22 is set if the test switch is not depressed. For testing, the test switch applies a constant logic 1 to shift register input line RIN and also removes gate GX control from flip-flop 22, so that successive trains of logic 1 signals are constantly shifted through the register, lighting all the LEDs, thereby also exercising (i.e. testing) some of the logic circuits as well as the LEDs. Upon release of the test button, the one-shots P1 and P2 clear the shift register before the next transmit pulse.

It will be apparent that a variety of changes may be made in the exemplary circuitry shown in accordance with well-known techniques. While the timing and synchronization of substantially all of the circuits of the preferred embodiment of FIG. 1 is shown controlled by digital counter CO, these functions, other than shifting of the shift register, can, if desired, be controlled in some respects in analog fashion, as is exemplified by the use of the one-shots P1 and P2 in FIG. 6b, for example. The TRG signal can be provided by a one-shot (not shown) triggered by a particular count condition of counter CO. Counter CO could, if desired, use a counting radix other than the binary one assumed to be used. Various different types of gates and flip-flops may be substituted for those shown in accordance with well-known principles. While the display is assumed to comprise a row of presently commercially-available light-emitting diodes of the gallium arsenide phosphide type, it will be apparent that equivalent visible elements, such as various forms of liquid crystals, may be substituted.

The embodiments of the invention in which an exclusive property or privilege is claimed are defined as follows:

1. Ultrasonic inspection apparatus, comprising, in combination: ultrasonic transducer means for repetitively applying pulses of ultrasonic energy to an object to be inspected and receiving reflected ultrasonic energy from said object to provide trains of first electrical signals; amplifying and detecting means for detecting those of said electrical signals of each train which have amplitudes exceeding a selected threshold value to provide respective logic signals; storage means having a plurality of stages for storing the logic signals resulting from said trains of signals with a distribution among said stages in accordance with their respective times of occurrence during a given train; and a linear array of light-emitting elements controlled by respective stages of said storage means to be illuminated in accordance with the signals stored in said storage means to provide an operator-observable display.

2. Apparatus according to claim 1 in which said amplifying and detecting means includes full-wave rectifying means, whereby those of said electrical signals having amplitudes exceeding said threshold value will provide a respective logic signal irrespective of their polarity.

3. Apparatus according to claim 1 wherein said amplifying and detecting means includes means for amplifying successive first electrical signals of each of said trains with a gain which increases during the time of occurrence of a given train.

4. Apparatus according to claim 1 wherein said amplifying and detecting means includes variable attenuator means for attenuating successive first electrical signals of each of said trains with an attenuation which decreases during the time of occurrence of a given train.

5. Apparatus according to claim 1 wherein said storage means comprises a shift register having an input line connected to receive said logic signals, and means for periodically shifting said shift register to store said logic signals in said shift register with a spacing in accordance with the time spacing of the first electrical signals detected to provide said logic signals.

6. Apparatus according to claim 1 including an oscillator, counter means connected to said oscillator to be repetitively re-cycled through a plurality of count conditions, first gating means responsive to the contents of said counter means for periodically activating said ultrasonic transducer means to apply pulses of ultrasonic energy to said object, said storage means comrising a shift register, and second gating means responsive to said oscillator and to said first gating means for applying shift pulses to shift said shift register.

7. Apparatus according to claim 1 wherein each of said logic signals stored in said storage means in response to one of said electrical signals exceeding said threshold value is arranged to illuminate a respective one of said light-emitting elements, and means for clearing said storage means to illuminate all of said light-emitting elements.

8. Apparatus according to claim 1 wherein said transducer means comprises a piezoelectric crystal and said apparatus includes high-voltage supply means having one terminal connected to a first terminal of said crystal, thyristor means having anode and cathode terminals and a gate lead, one of said terminals of said thyristor means being connected to said first terminal of said crystal, a resistance and a capacitor connected in series between the terminal of said high-voltage supply means and a second terminal of said crystal, the other of said terminals of said thyristor means being conneced to the junction between said resistance and said capacitor, and means for periodically energizing said gate lead of said thyristor means.

9. Apparatus according to claim 1 having a battery; converter means powered by said battery to provide a transducer supply voltage exceeding the voltage of said battery; and means for disabling said converter means while said trains of first electrical signals are being received.

10. Apparatus according to claim 1 having a battery, a regulated power supply powered by said battery and operable to supply operating voltage to said storage means, and test switch means for conditioning said storage means to illuminate all of said light-emitting elements, said power supply including means responsive to a lowered battery charge level for removing said operating voltage from said storage means, whereby occurrence of said lowered battery charge level will cause said operating voltage to be removed from said storage means, thereby causing said light-emitting elements to turn off to indicate said lowered battery charge level.

11. Apparatus according to claim 1 having means for repetitively varying the magnitudes of said pulses of ultrasonic energy applied to said object over successive time intervals embracing groups of said pulses.

12. Apparatus according to claim 1 having means for repetitively varying the gain with which said trains of first electrical signals are processed over successive time intervals each embracing plural trains, thereby to illuminate said light-emitting elements with intensities which when averaged over said time interval are commensurate with the amplitudes of reflections of ultrasonic energy at respective depths within said objects.

13. Apparatus according to claim 1 having means for repetitively varying said threshold value over successive time intervals each embracing a plurality of said trains of first electrical signals.

14. Apparatus according to claim 1 having scale indicia provided adjacent said array of light-emitting elements and calibrated in terms of units of length, whereby the depths within said object from which said ultrasonic energy is reflected will be indicated adjacent various ones of said light-emitting elements.

15. Apparatus according to claim 5 having means synchronized with said ultrasonic transducer to activate said means for periodically shifting said shift register upon the applying of each pulse of ultrasonic energy to said object, and switching means responsive to the shifting of a predetermined one of said logic signals stored in said shift register to a predetermined stage of said register for de-activating said means for periodically shifting said shift register.

16. Apparatus according to claim 5 wherein said means for periodically shifting said shift register is operative to shift said register at a plurality of successive time-spaced instants, and wherein said detecting means includes means responsive to an echo signal which occurs prior to one of said time-spaced shifting instants for providing one of said logic signals at the next succeeding one of said shifting instants.

17. Apparatus according to claim 5 wherein said means for periodically shifting said shift register is operative to shift said register at a plurality of successive time-spaced instants, and wherein said detecting means includes means responsive to an echo signal which bridges one of said instants for ignoring the portion of said echo signal which occurs after said one of said instants any any further echo signal which occurs during a predetermined time after said one said instants.

18. Apparatus according to claim 5 having switch means for varying the shifting rate of said shift register.

19. Apparatus according to claim 5 having means operable prior to transmission of each applied pulse of ultrasonic energy for conditioning each stage of said storage means to turn off the respective light-emitting element which is controlled by such stage.

20. Apparatus according to claim 5 having means responsive to the shifting of a selected one of said logic signals detected from a given one of said trains after a predetermined time interval following the transmission of the pulse of ultrasonic energy causing said given one of said trains for terminating shifting of said shift register.

21. Apparatus according to claim 15 having selector switch means for selecting which of said stages of said register functions as said predetermined stage.

22. The method of indicating a density gradient profile of a portion of an animal comprising the steps of periodically transmitting ultrasonic energy to said portion and receiving reflected energy therefrom in the form of trains of electrical signals; detecting those of said electrical signals of each train having amplitudes in excess of a threshold value to provide logic signals; storing said logic signals from each train in multi-stage register means with a spacing in accordance with their times of occurrence during a respective train; and illuminating respective ones of a linear array of light-emitting elements in accordance with the logic signals stored in said register means to provide an operator-observable display.

23. Apparatus for indicating a density gradient profile of a portion of an animal, comprising, in combination: means for periodically transmitting ultrasonic energy to said portion and receiving reflected energy therefrom to produce trains of electrical signals; means of detecting those of said electrical signals of each train having amplitudes exceeding a threshold value to provide logic signals; storage means having a plurality of stages for storing said logic signals detected from each train with a distribution of said logic signals among said stages in accordance with the times of occurrence of said logic signals during said train; and a linear array of light-emitting elements, each of said light-emitting elements being connected to be illuminated by storage of one of said logic signals in a respective one of said stages of said storage means, thereby to provide an operator-observable display.

24. Apparatus according to claim 1 wherein said ultrasonic tranducer means comprises a crystal operative to repetitively apply said pulses of ultrasonic energy to said object and to receive reflected ultrasonic energy from said object to provide one of said trains of first electrical signals after each of said pulses of ultrasonic energy is applied to said object.

25. Apparatus according to claim 1 wherein said amplifying and detecting means includes an amplifier for amplifying each of said trains of first electrical signals to provide second electrical signals.

26. Apparatus according to claim 25 wherein said amplifying and detecting means includes a threshold detector for detecting each of said second electrical signals having an amplitude exceeding said threshold value to provide a plurality of said logic signals sequentially.

27. Apparatus according to claim 26 wherein said storage means comprises a plurality of cascaded storage stages including a first stage, said first step being connected to receive each of said logic signals.

* * * * *